(12) United States Patent
Shau et al.

(10) Patent No.: US 10,448,004 B1
(45) Date of Patent: Oct. 15, 2019

(54) ERGONOMIC PROTECTIVE EYEWEAR

(71) Applicants: Alexander Shau, Palo Alto, CA (US); Jeng-Jye Shau, Palo Alto, CA (US)

(72) Inventors: Alexander Shau, Palo Alto, CA (US); Jeng-Jye Shau, Palo Alto, CA (US)

(*) Notice: Subject to any disclaimer, the term of this patent is extended or adjusted under 35 U.S.C. 154(b) by 0 days.

(21) Appl. No.: 15/984,383

(22) Filed: May 20, 2018

(51) Int. Cl.

| | |
|---|---|
| *H04N 13/344* | (2018.01) |
| *H04N 13/398* | (2018.01) |
| *H04N 13/361* | (2018.01) |
| *H04N 7/15* | (2006.01) |
| *H04N 5/44* | (2011.01) |
| *G02B 27/01* | (2006.01) |
| *G02C 7/10* | (2006.01) |
| *A61B 90/00* | (2016.01) |
| *H04N 13/239* | (2018.01) |
| *A61B 90/50* | (2016.01) |
| *H04N 5/45* | (2011.01) |
| *G06T 7/60* | (2017.01) |
| *H04N 5/225* | (2006.01) |

(52) U.S. Cl.
CPC ......... *H04N 13/344* (2018.05); *A61B 90/361* (2016.02); *G02B 27/0172* (2013.01); *G02C 7/104* (2013.01); *H04N 5/4403* (2013.01); *H04N 7/15* (2013.01); *H04N 13/239* (2018.05); *H04N 13/361* (2018.05); *H04N 13/398* (2018.05); *A61B 2090/372* (2016.02); *A61B 2090/373* (2016.02); *A61B 2090/502* (2016.02); *G02B 2027/0134* (2013.01); *G02B 2027/0138* (2013.01); *G02B 2027/0178* (2013.01); *G06T 7/60* (2013.01); *H04N 5/2256* (2013.01); *H04N 5/45* (2013.01); *H04N 2005/4432* (2013.01); *H04N 2213/001* (2013.01); *H04N 2213/002* (2013.01); *H04N 2213/008* (2013.01)

(58) Field of Classification Search
CPC ...... H04N 7/15; H04N 5/2256; H04N 13/344; H04N 13/361; H04N 13/398; H04N 2213/008; A61B 90/61; A61B 2090/372; A61B 2090/373; G02B 27/0172; G02C 2027/0134; G02C 7/104
USPC .......................................................... 348/62
See application file for complete search history.

(56) References Cited

U.S. PATENT DOCUMENTS

| | | | |
|---|---|---|---|
| 7,542,204 B2 | 6/2009 | Fante et al. | |
| 9,094,576 B1* | 7/2015 | Karakotsios | ........... H04N 7/157 |
| 9,465,235 B2 | 10/2016 | Chang | |
| 9,690,119 B2* | 6/2017 | Garofolo | ................... G02C 7/14 |
| 9,729,767 B2* | 8/2017 | Longbotham | ........ G02B 27/017 |
| 2006/0001740 A1 | 1/2006 | Fujie et al. | |
| 2012/0130223 A1* | 5/2012 | Reicher | ................. G06F 19/321 |
| | | | 600/407 |
| 2015/0346816 A1* | 12/2015 | Lee | ........................ H04N 7/142 |
| | | | 345/8 |
| 2016/0104453 A1* | 4/2016 | Borenstein | .......... H04N 13/257 |
| | | | 348/62 |

(Continued)

*Primary Examiner* — Maria El-Zoobi (57) ABSTRACT

Using two or more cameras attached to the protective eyewear, three-dimensional views with accurate and natural depth perception of the working area can be displayed for users, so that the user can maintain healthy sitting or standing posture while working on patients or objects located below horizontal eye level. Additional functions including eye protection, zoom-in, zoom-out, on-off, lighting control, overlapping, and teleconference capabilities are also supported using electronic, video and audio devices attached to the eyewear.

20 Claims, 7 Drawing Sheets

(56) References Cited

U.S. PATENT DOCUMENTS

2018/0097998 A1* 4/2018 Yuan .................. H04N 5/76
2019/0011612 A1* 1/2019 Mastrangelo ............ G02B 3/14

* cited by examiner

ERGONOMIC PROTECTIVE EYEWEAR

BACKGROUND OF THE INVENTION

This application relates to protective eyewear of the type worn by medical, surgical, dental, and other healthcare professionals, and particularly eyewear that allow users to maintain ideal, healthy working posture while simultaneously providing ideal working vision. The terminology "eyewear" includes "eye glasses", "loupes", "goggles", "safety glasses", "smart glasses", "protective eyewear", and other types of wearable devices worn over the eyes.

Figure 1A:
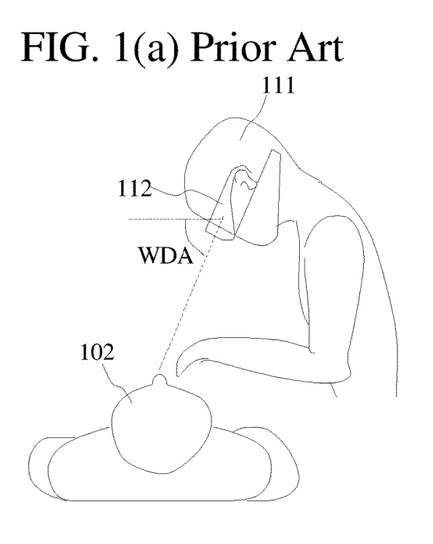
FIG. 1(a) is a symbolic diagram that shows a doctor treating a patient while wearing traditional, prior art protective eyewear.

Doctors, Surgeons, Dentists, and other healthcare professionals often need to work on a patient or device that requires use of the hands below the normal level of eye sight. FIG. 1(a) illustrates an example of a doctor (111) working on a patient (102) using traditional protective eyewear (112). The Working Declination Angle (WDA), is defined as the angle between the horizontal plane and the line from the viewer's eyes to the working area. Here, the horizontal plane is used to approximate a viewer's unstrained, straight viewing direction while sitting or standing with healthy posture. The Working Declination Angle (WDA) is often larger than 60 degrees. Using traditional protective eyewear (112), the doctor (111) needs to bend the head, neck, and back, and/or use excessive downward eye tilt in order to view the working area clearly, as shown in FIG. 1(a). The doctor (111) frequently needs to hold this uncomfortable and unhealthy posture for long periods of time throughout a working day. Such unfavorable working posture frequently results in back, neck, shoulder, and/or eye strain, causing fatigue that can degrade the quality of the operation and also lead to chronic health problems for the professional.

Figure 1B:
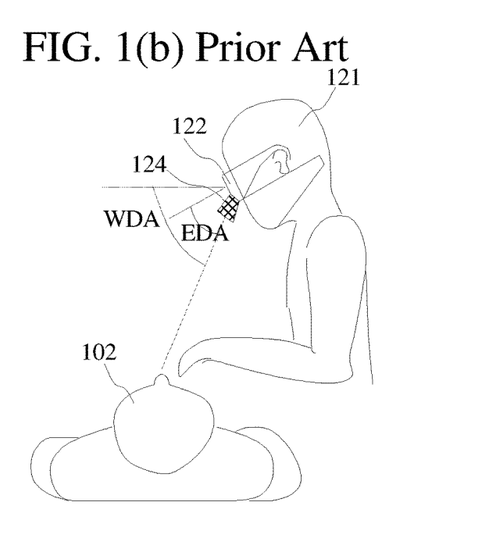
FIG. 1(b) is a symbolic diagram that shows a doctor treating a patient while wearing a prior art eyewear that has magnification eye pieces, or loupes, with an eyewear declination angle.

The most common prior art solution for this problem is to wear specialized eyewear (122) using loupes or magnification eye pieces (124) arranged in an Eyewear Declination Angle (EDA), as illustrated in FIG. 1(b). The Eyewear Declination Angle (EDA) is defined as the angle between the eyewear viewing direction and the viewing direction of the image capturing device(s) on the eyewear, as illustrated by the example in FIG. 1(b). The eyewear viewing direction is defined as the unstrained, straight viewing direction through the eyewear, approximately parallel to the horizontal plane when the user sits or stands with ideal, healthy posture. An image capturing device can be an eye piece, camera, or other optical and/or electronic device. For the case in FIG. 1(b), the required working declination angle (WDA) is the same as that in FIG. 1(a), while the eyewear declination angle (EDA) of the magnification eye pieces (124) allows the doctor (121) to view working areas with less bending of the neck and back, as illustrated in FIG. 1(b). However, due to space limitations, the achievable eyewear declination angle (EDA) of the magnification eye pieces (124) is typically limited to be smaller than the required working declination angle (WDA). Furthermore, use of such specialized eyewear (122) still requires the user to strain the eyes in a downward direction. It provides a partial solution to the problem, but it does not solve the problem adequately. Professionals are still required to strain the back, neck, shoulders and/or eyes to achieve proper working vision, though to a lesser degree when compared with the traditional protective eyewear in FIG. 1(a).

Chang in U.S. Pat. No. 9,465,235 disclosed a through-the-lens loupe with improved eyewear declination angle. Holes are opened on the viewing windows of the eyewear to allow larger built-in eyewear declination angles. However, the angle is still not large enough to allow the doctor to maintain ideal ergonomic posture while working.

Fante et al. in U.S. Pat. No. 7,542,204 disclosed a method to improve eyewear declination angle using optical deflectors. The resulting microscopes are larger and heavier than the prior art example in FIG. 1(b). Fante may help reduce problems caused by the working declination angle, but the added weight of the deflectors may also cause ergonomic problems.

Fujie et al in U.S. patent application Ser. No. 11/090,820 disclosed a system for dental diagnosis and treatment that includes an intraoral camera which can capture moving images in the patient's oral cavity, and the camera can be fixed near the patient's mouth. The image captured by the intraoral camera is displayed on a TV screen or monitor installed at a position where the dentist can see. Using video image processing methods, the system can invert the image in the vertical direction and reverse the image in the lateral direction. The capabilities of Fujie's image processing are limited to image reversion. Additionally, the image is taken from an intraoral camera directly facing the mouth of a patient, which is not the same position of view from which dentists are familiar with working. Using this system, dentists need to operate with a different field of view than that with which they are trained. Furthermore, images displayed on the monitor are two-dimensional views which lack depth perception. Depth perception is defined as the visual ability to perceive the world in three dimensions, the ability to judge the distance of objects, and the ability to perceive the spatial relationship of objects at different distances. This information is critical for operations requiring precise hand-eye coordination. Fujie may help reduce the ergonomic problems caused by unfavorable posture, but with this system, users need to spend time re-training themselves to operate in an unfamiliar manner.

Garofolo et al in U.S. Pat. No. 9,690,119 disclosed a device that is equivalent to a virtual reality eyewear with an added centered camera system. Images of a working area captured by the centered camera are displayed on the screen of the virtual reality eyewear, allowing the user to view the working area in an ergonomically healthy posture. However, a centered optical system cannot provide three-dimensional views with accurate depth perception. It lacks the features to support professional operations that require a high level of hand-eye coordination. This complicated high-technology virtual reality eyewear also creates a working environment that is not familiar for doctors. The added weight of the virtual reality eyewear also can cause ergonomic problems.

These prior art devices provide partial solutions to the problem, but they do not solve the problem adequately. It is therefore desirable to provide eyewear for medical, surgical, dental, and other healthcare professionals that can allow them to treat patients from the same doctor-patient positions with which they have been trained, while simultaneously operating with ideal ergonomic posture. Other professionals who are required to work below the normal level of eye sight, such as dental hygienists, veterinarians, and laboratory technicians, will also benefit from this invention. It is essential that the view provided by the eyewear can accurately represent the three-dimensional view with accurate and natural depth perception, to which healthcare professionals are accustomed. It is additionally essential that the eyewear can provide additional working aids using image processing technology and audio signal processing technology.

SUMMARY OF THE PREFERRED EMBODIMENTS

A primary objective of the preferred embodiments is, therefore, to provide eyewear that allow users to view working areas below the horizontal plane while maintaining ideal, healthy sitting or standing posture. Another primary objective is to provide eyewear that allow users to view three-dimensional video images of working areas with accurate and natural depth perception. Another primary objective is to provide eyewear that allow professionals to work from familiar doctor-patient working positions with which they have been trained. Other objectives are to provide functions including eye protection, zoom-in, zoom-out, on-off, lighting control, overlapping, and teleconference capabilities using electronic, video and audio devices attached to the eyewear. These and other objectives can be achieved by attaching two or more cameras to the eyewear, along with video display devices, audio devices, lighting, and other supporting components as illustrated in the following paragraphs. Another objective is to provide active noise cancellation capability on accessory earphones.

While the novel features of the invention are set forth with particularly in the appended claims, the invention, both as to organization and content, will be better understood and appreciated, along with other objects and features thereof, from the following detailed description taken in conjunction with the drawings.

DETAILED DESCRIPTION OF THE PREFERRED EMBODIMENTS

Figure 2A:
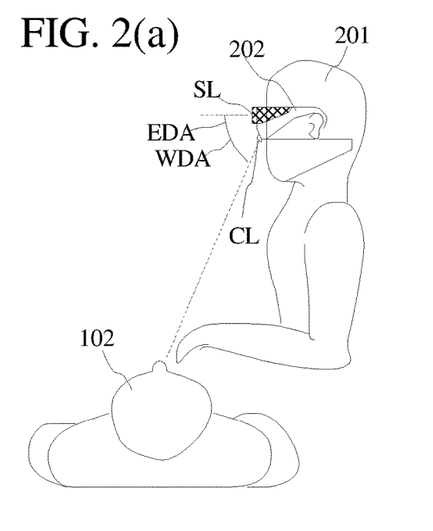
FIG. 2(a) is a symbolic diagram that shows a doctor wearing an exemplary embodiment of this patent application.
Figure 3A:
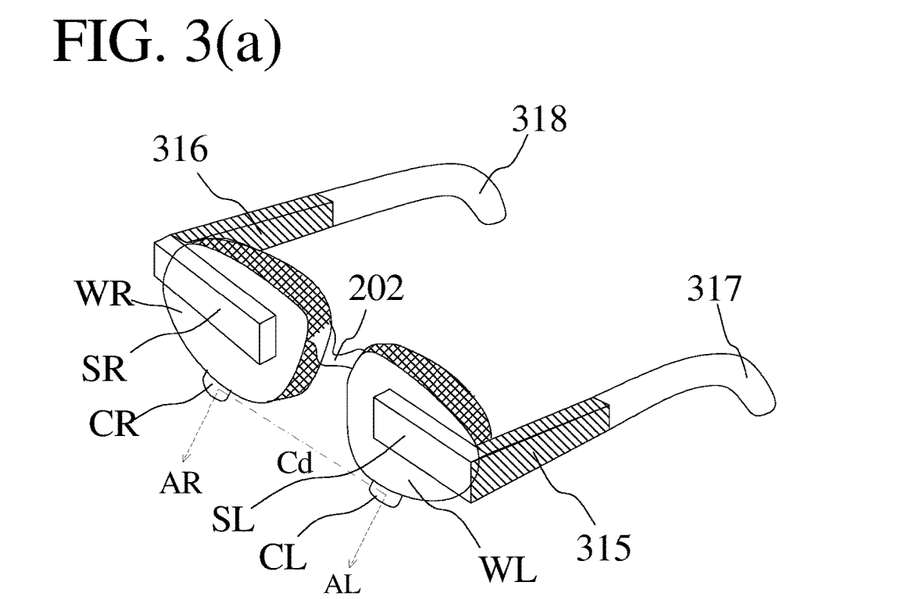
FIG. 3(a) illustrates exemplary structures of the eyewear in FIG. 2(a)

FIG. 2(a) is a symbolic diagram that shows a doctor (201) wearing an exemplary embodiment of the eyewear (202) in this patent application. FIG. 3(a) illustrates exemplary structures of the eyewear in FIG. 2(a). This eyewear (202) comprises a pair of viewing windows (WL, WR). The user's right eye views through the right viewing window (WR), and the user's left eye views through the left viewing window (WL). A right-eye-side camera (CR) is placed on or near the bottom of the right viewing window (WR), and a left-eye-side camera (CL) is placed on or near the bottom of the left viewing window (WL), as shown in FIG. 3(a). These cameras (CR, CL) can be equipped with built-in light sources and flashes aligned with the cameras (CR, CL). The light sources can also have color filters that allow the user to change the wavelengths of emitted light. Users have the option to detach these cameras (CR, CL). A right-eye video display device (SR) is placed in front of the right viewing window (WR), and a left-eye video display device (SL) is placed in front of the left viewing window (WL), as illustrated in FIG. 3(a). Users have the option to detach these video display devices (SR, SL), turn them off, or move them out of sight. It is desirable to make the video display devices (SR, SL) using materials that are transparent or partially transparent while not in use. This allows for normal everyday vision through the eyewear with the video display devices (SR, SL) still in place, when the electronic functions of the eyewear have been switched off. The video display devices (SR, SL) can also be built-in to become part of the viewing windows (WR, WL) themselves. The distance (Cd) between two cameras (CR, CL) is typically adjusted to be about the same as the distance between the pupils of the user. The viewing direction (AR) of the right-eye-side camera (CR) and the viewing direction (AL) of the left-eye-side camera (CL) can be adjusted not only in a vertical direction but also in a horizontal direction with total freedom. AR and AL are typically adjusted to have the same angle relative to the eyewear viewing direction while focusing on a targeted working area, as illustrated in FIG. 3(a). The Eyewear Declination Angle (EDA) of the eyewear (202) is defined as the angle between the eyewear viewing direction and the viewing directions (AR, AL) of these cameras (CR, CL). These viewing directions (AR, AL) can be adjusted manually or automatically. Unlike prior art eyewear, there is no space limitation in adjusting the viewing directions (AR, AL) of the cameras (CR, CL). Typically, the eyewear declination angle (EDA) of the eyewear is adjusted to be about the same as the working declination angles (WDA) shown in FIGS. 1(a, b), so that EDA=WDA, and the doctor (201) can operate in healthy sitting or standing posture, as illustrated in FIG. 2(a). The geometry of these cameras (CR, CL) allows users to view three-dimensional video images of working areas on the video display devices (SR, SL) with accurate and natural depth perception. The eyewear allows doctors to work from familiar doctor-patient working positions with which they have been trained. Supporting components, such as video signal processing units, optical control units, audio signal processing units, memory devices, communication circuits, or power sources, can be placed in the sides (315, 316) of the eyewear, in the front of the eyewear, or placed externally. The total weight of the eyewear (202) is light enough so that it is not burdensome to the user.

Figure 3B:
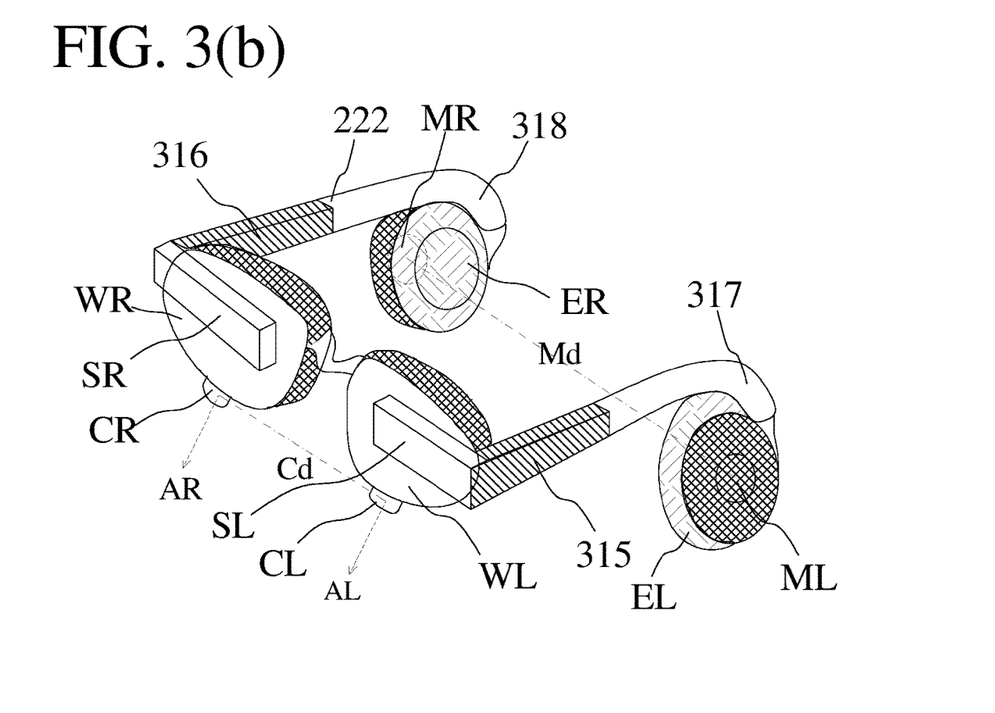
FIG. 3(b) illustrates exemplary structures of the eyewear in FIG. 2(b)
Figure 3C:
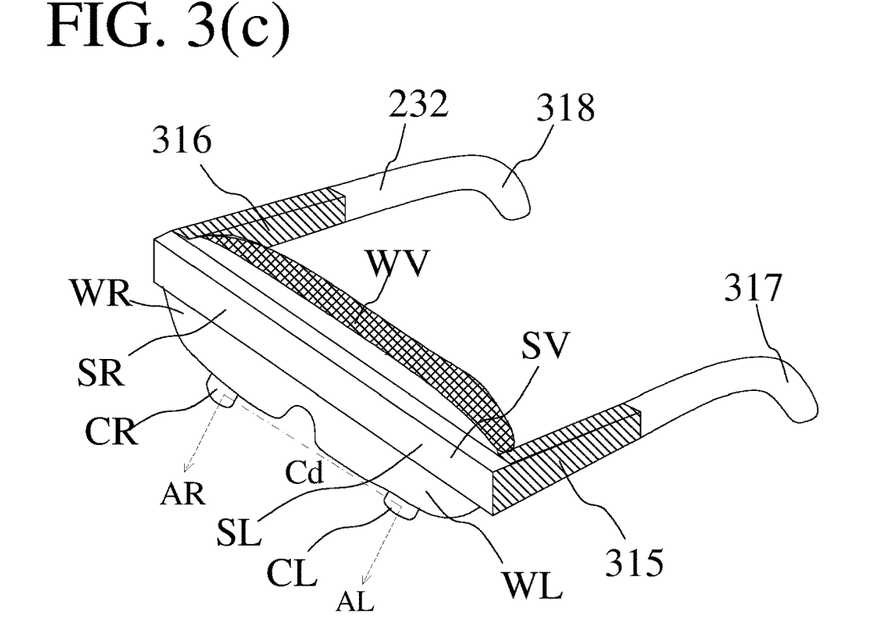
FIG. 3(c) illustrates exemplary structures of an eyewear (232) of this patent application that has an integrated viewing window (WV) and an integrated video display (SV)

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in FIGS. 3(a, b) the right-eye and left-eye video display devices (SR, SL) exist as separate devices. However, the video display device(s) of this patent application can also exist as one single video display device (SV) that has separate display areas (SR, SL) for the right and left eyes, as shown in FIG. 3(c). Likewise, in FIGS. 3(a, b) the right and left viewing windows (WR, WL) are separate structures, but can also exist as one single viewing window (WV) that has separate areas (WR, WL) for the right and left eyes, as shown in FIG. 3(c). The video display devices (SR, SL, SV) can be separate structures from the viewing windows (WR, WL, WV), or can also be built-in to become part of the viewing windows themselves.

Figure 2B:
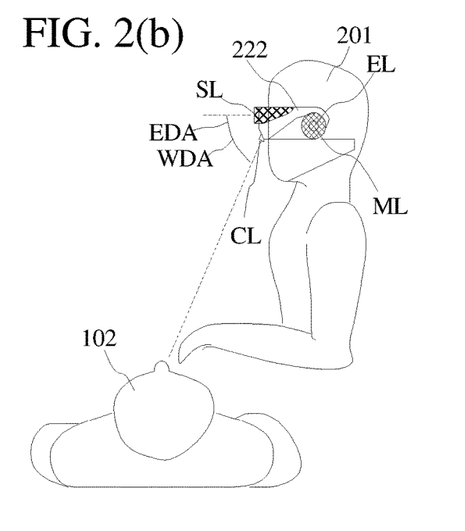
FIG. 2(b) is a symbolic diagram that shows a doctor wearing another exemplary embodiment of this patent application that is equipped with audio devices.

For another example, FIG. 2(b) is a symbolic diagram that shows a doctor (201) wearing an exemplary embodiment of an eyewear (222) of this patent application that is equipped with audio devices (EL, ML). FIG. 3(b) illustrates exemplary structures of the eyewear in FIG. 2(b). This eyewear (222) comprises the same components as the eyewear (202) in FIG. 3(a), but with an added pair of earphones (ER, EL) and a pair of microphones (MR, ML), as shown in FIG. 3(b). The distance (Md) between these two microphones (MR, ML) can be approximately the same as the distance between the ears of the user, or the microphones (MR, ML) can also extend closer to the mouth of the user. The user may speak commands to control the on-off, zoom-in, zoom-out, eyewear declination angle, lighting, wavelength filtering, camera distance, overlapping images, and various other functions of the eyewear. Alternatively, the user may also control the eyewear through use of a connected or remotely controlled external device.

Figure 4A:
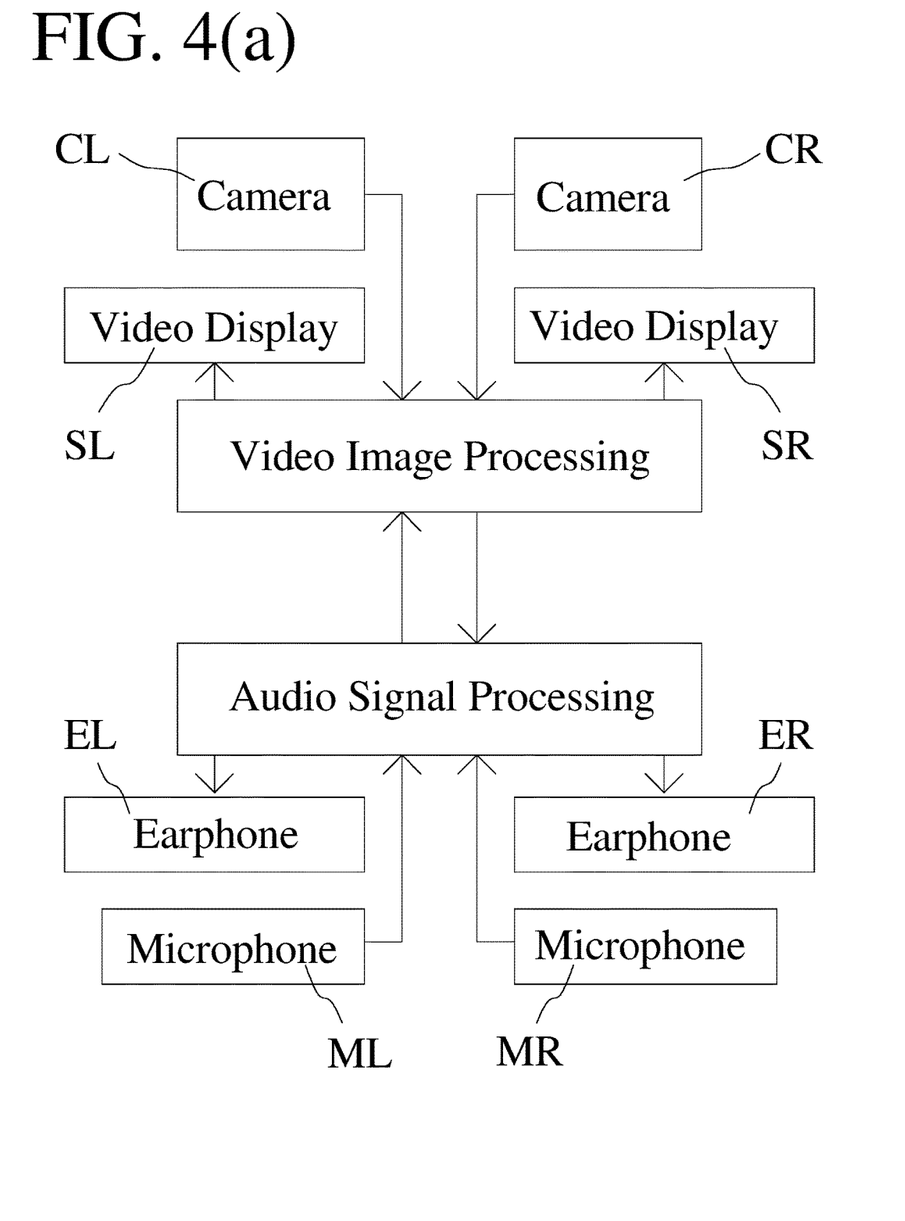
FIG. 4(a) is a simplified symbolic block diagram illustrating the structures of the eyewear (222) in FIG. 3(b)

FIG. 4(a) is a simplified symbolic block diagram illustrating the structures of the eyewear (222) in FIG. 3(b). The right-eye-side camera (CR) and the left-eye-side camera (CL) capture the right and left views that the doctor (201) wishes to see. These views are then processed and displayed on the right-eye video display (SR) and the left-eye video display (SL) in real-time. Display in real-time means that the delay time from the moment images are captured by the cameras to the moment in which the images are shown on the video displays is short enough so that the user cannot feel significant delay. For example, if the delay time due to image processing is shorter than 0.1 second, then there should be less than 0.1 second between the moment the cameras capture an image to the moment the image is shown on the video displays. The distance (Cd) between the two cameras (CR, CL) is typically about the same as the distance between the pupils of the doctor (201). The viewing directions (AR, AL) of the two cameras (CR, CL) are typically adjusted to have the same eyewear declination angle (EDA) as the working declination angle (WDA). Therefore, when the doctor (201) views the video displays (SR, SL) through both of his eyes, he sees a three-dimensional view with the same depth perception as if the doctor were looking downward with his own eyes. The video displays (SR, SL) are located in front of the viewing windows (WR, WL) at or near a horizontal orientation, so that the user can view the displays of the working area with minimal to no strain of the eyes, while maintaining healthy sitting or standing posture as illustrated in FIGS. 2(a, b).

While the preferred embodiments have been illustrated and described herein, other modifications and changes will be evident to those skilled in the art. It is to be understood that there are many other possible modifications and implementations so that the scope of the invention is not limited by the specific embodiments discussed herein. Eyewear of this patent application allows the users to view their preferred working three-dimensional views with proper depth perception, while maintaining ergonomically healthy posture. Using video image processing technology and audio signal processing technology, the eyewear can also support many other functions.

Figure 4B:
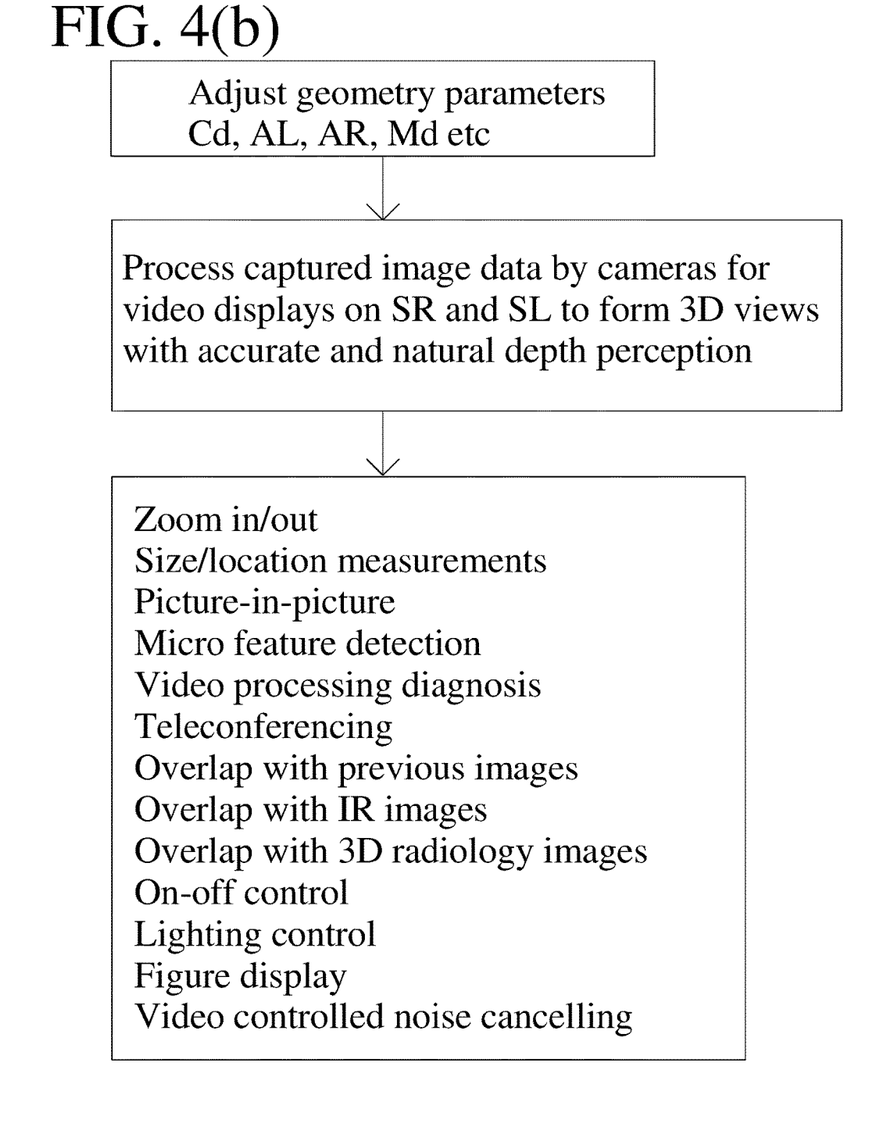
FIG. 4(b) is a simplified flow chart illustrating exemplary video image processing procedures for one embodiment of this patent application.

FIG. 4(b) is a flow chart illustrating exemplary signal processing procedures for the eyewear (222) in FIG. 3(b). The user adjusts geometry parameters such as the distance (Cd) between two cameras (CR, CL), viewing directions of cameras (AR, AL), the distance (Md) between the two microphones (MR, ML), the working distance between the eyewear and the user's hands, and other related geometry parameters. Those parameters can be adjusted manually or automatically. Knowing these geometry parameters, image processing technology is able to calculate and display realistic views from the video data captured by the cameras (CR, CL). The user can zoom in or zoom out as he/she wishes, while image processing can display three-dimensional views with correct magnification and depth perception on the video displays (SR, SL), all with the user maintaining healthy upright posture. The on-off, zoom in-zoom out, and other command features can be triggered by voice recognition using microphones (MR, ML) supported by audio signal processing technology. These commands can also be given without voice control, from an external device that is either attached to the eyewear or remotely configured. Given geometry parameters, image processing can also measure the size of different objects that the user chooses to measure. It is also able to display 360-degree views of an object the user chooses. Image signal processing can help the user detect and highlight features that are difficult to detect with the naked eye, such as micro-fractures, small cavities, or discolored areas. The user can take pictures with the cameras, and save these pictures as part of the patient's record for future reference.

Figure 5:
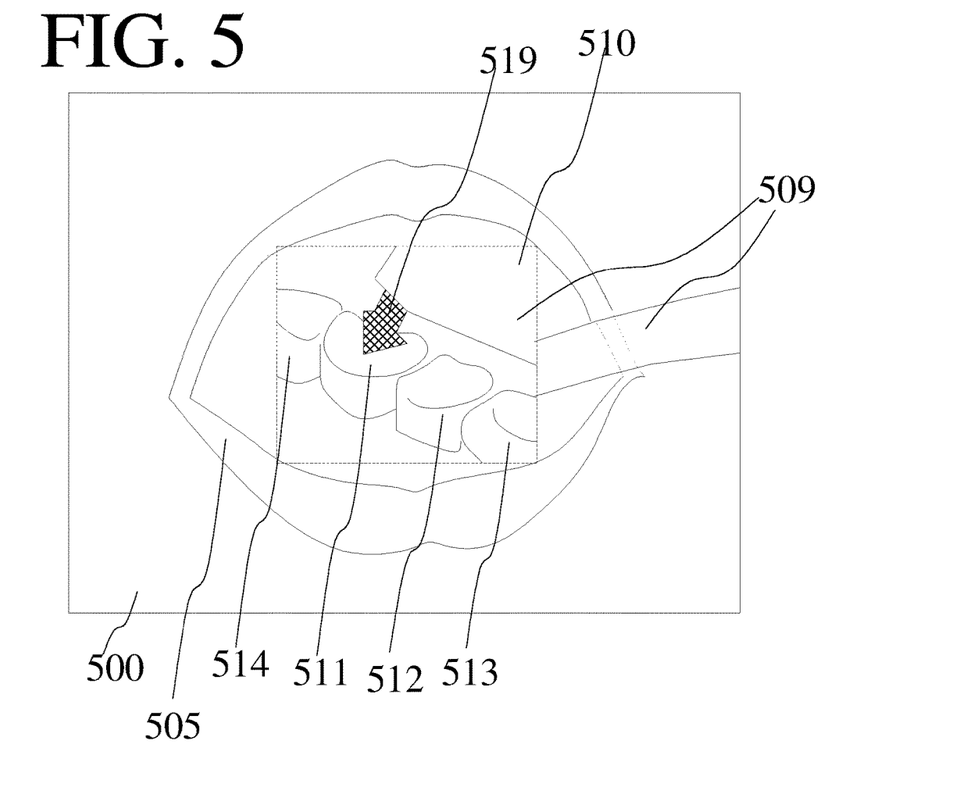
FIG. 5 shows an exemplary embodiment of the picture-in-picture feature of the eyewear.

Video image processing can also have a picture-in-picture function. As an illustration of this function, a relatively low magnification picture (500) can be displayed on the periphery of the screen, showing the surrounding features of the patient (505) and working environment, while a high magnification picture (510) of a dental drill (509) and a tooth (511) can be displayed near the center of the screen as enclosed by the dashed lines in FIG. 5. In this center picture (510), a dentist can see a magnified view of the teeth (511-514), and the tip of a dental drill (519) that is drilling a cavity on a tooth (511). Such a picture-in-picture option allows the user to maintain broad peripheral vision of his surroundings while simultaneously focusing on a specific working area with high magnification. Notes, previous pictures, x-rays, figures, tables, or other forms of data can also be displayed on the video display devices (SR, SL) while the user is in operation.

The user can display previous patient images on the screen and use video image processing to overlap and compare areas of interest. Overlapping infrared images with the camera views can detect abnormalities that are not visible with the bare eye. Video image processing can also overlap previously recorded three-dimensional radiology images, such as those from computed tomography scans, magnetic resonance imaging, ultrasounds, and other types of diagnostic imaging modalities, with current viewing images to help a doctor locate radiology findings in current views accurately. The eyewear also can support teleconferencing. Colleagues in remote areas can see what the operator sees, as if viewing through the operator's own eyes. At the same time, the operator can speak with colleagues who are watching through the cameras, through use of telecommunication. Movies of any recorded video can be documented as well.

Audio signal processing can support active noise cancelling using the microphones (MR, ML) and the earphones (ER, EL).

While the preferred embodiments have been illustrated and described herein, other modifications and changes will be evident to those skilled in the art. It is to be understood that there are many other possible modifications and implementations so that the scope of the invention is not limited by the specific embodiments discussed herein. For example, in FIGS. 3(a-c) there are only two cameras (CR, CL) included in the illustrations, while three or more cameras can be used to improve accuracy of video signal processing. The cameras can be placed on or near the bottom of the eyewear, while the cameras also can be placed in a multitude of other locations as well. Light sources can be built into the cameras (CR, CL), or placed on many other different locations of the eyewear. For example, light sources may be placed immediately adjacent to the cameras or on the bridge of the frame. The size, shape and design of the eyewear may also vary to suit the user. The viewing windows (WR, WL, WV) of the eyewear may be transparent or may also contain filters to protect against eye-damaging wavelengths of light, such as those wavelengths emitted by various dental lasers. Such filtering options may be turned on/off and controlled using an attached controller, a remote control, or with voice commands. Wavelength filters may be built into the viewing windows, or may also be separately attachable to the viewing windows. Different viewing windows with varying filtering properties may also be detachable and replaceable within the same eyewear.

Figure 3D:
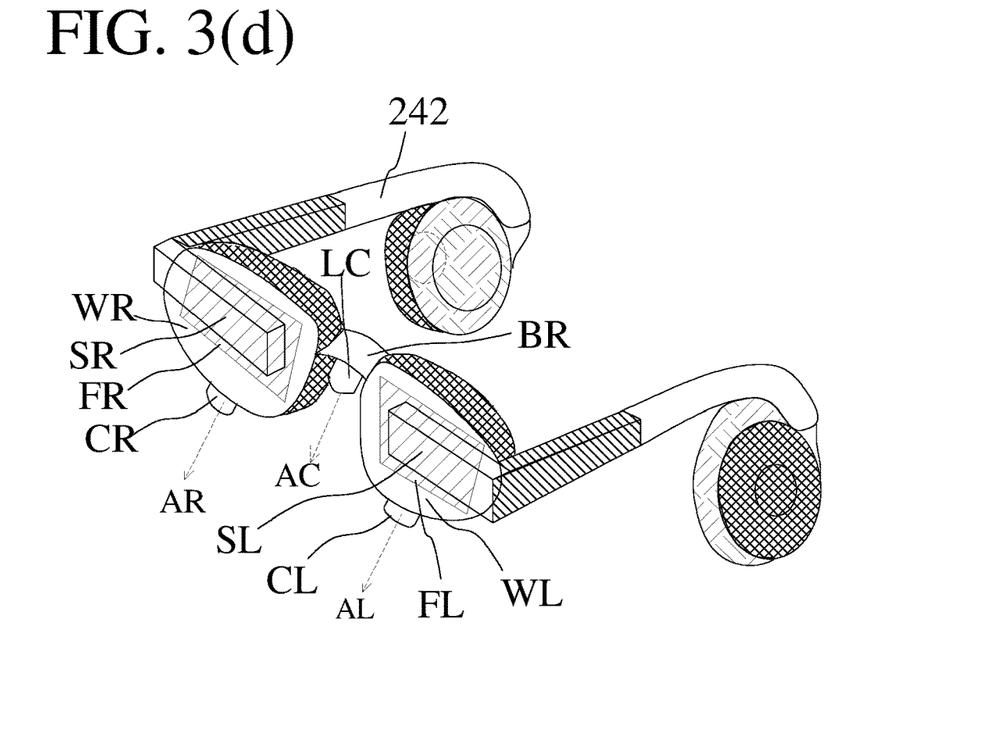
FIG. 3(d) illustrates exemplary structures of an eyewear (242) of this patent application that has an additional light source (LC) and protective light filters (FR, FL)

FIG. 3(d) illustrates exemplary structures of an eyewear (242) that comprises the same components as the eyewear (222) in FIG. 3(b), but with an added light source (LC) that is attached under the center bridge (BR) of the eyewear (242), and with a pair of sight filters (FR, FL) that are located in front of the viewing windows (WR, WL).

Figure 4C:
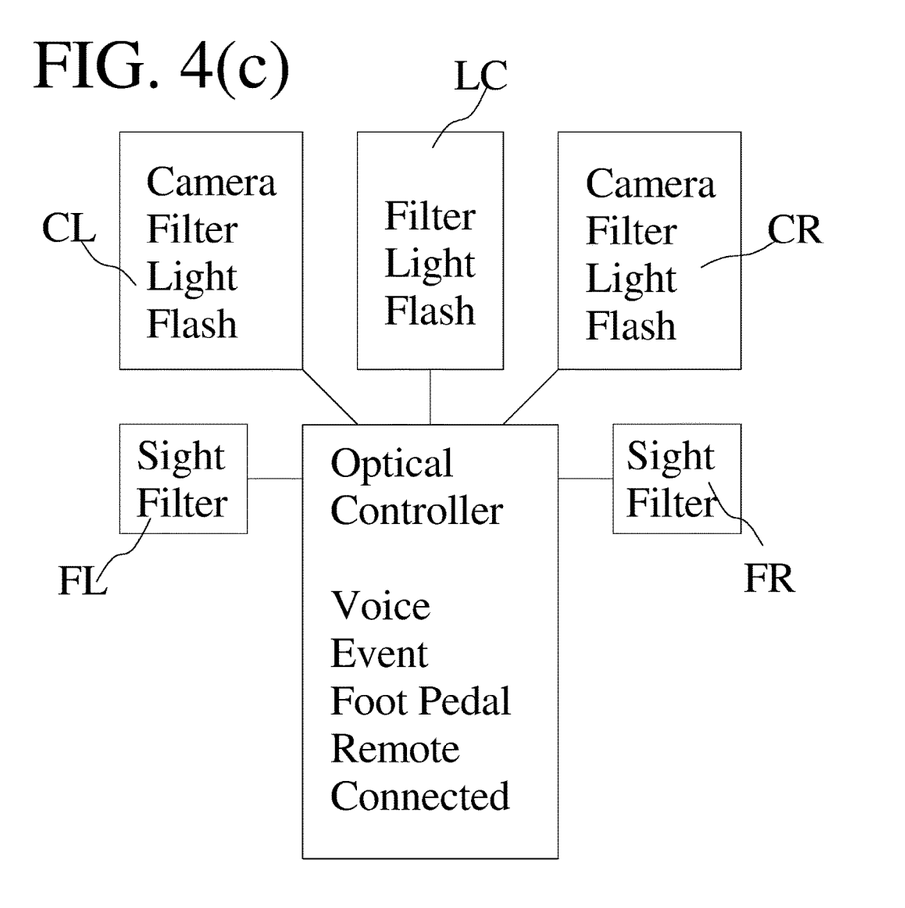
FIG. 4(c) is a simplified symbolic block diagram for an exemplary optical controller of the eyewear (242) in FIG. 3(d)

FIG. 4(c) is a simplified symbolic block diagram for an exemplary optical controller of the eyewear (242) in FIG. 3(d). Each camera (CR, CL) on the eyewear (242) can feature a light source, light filter, and/or camera flash. A light source built into or placed near a camera can be aligned to provide proper illumination for the views captured by the camera. The light sources can additionally have light filters. For example, a light filter can make the light source illuminate with orange-colored or yellow-colored lighting. In dentistry, light filters are especially important, for reasons described in the following paragraph. As another practical example, light filters can also serve to filter out all wavelengths outside of the infrared (IR) range, thus allowing a camera to capture IR images. A camera flash is also useful for taking pictures, especially in areas with poor illumination. The center light source (LC) can also have a light filter and/or camera flash. The viewing direction (AC) of the center light source (LC) is adjustable. Typically, this device viewing direction (AC) is adjusted to be about the same as that (AR, AL) of the cameras (CR, CL), but it also can be different. The sight filters (FR, FL) that are located in front of the viewing windows (WR, WL) or built into the viewing windows are used to protect the professional's eyes from harmful wavelengths of light. These optical components (CR, CL, LC, FR, FL) can be controlled manually or automatically. They can be controlled by voice activated commands, by a connected controller, or by a remote control. A remote control can even take the form of a foot pedal, which can be controlled with the feet while the user is busy with his/her hands. The optical components can also be activated by event-driven control. As a couple of examples for event-driven control, camera flashes may be activated when pictures are taken, or sight filters (FR, FL) may be activated when nearby harmful wavelengths of light are detected.

The lighting emitted by the eyewear can be turned on/off, changed into different levels of brightness, filtered, or changed into other modes. In dentistry, filtering is especially important because when normal lighting is shone on a tooth-colored filling, the filling often hardens prematurely while the dentist is still trying to pack the filling into the tooth. For this reason, normal lighting is often altered using a filter placed over the light source when the dentist is working with light-polymerized dental materials. Such filters eliminate the wavelengths of light which cause premature hardening of the filling material. It is therefore important that the lighting emanating from the eyewear in this application can be adjusted quickly and easily by the dentist, depending on the situation. For example, a dentist may want to work with normal bright lighting while drilling on a tooth, but then switch to a filtered lighting mode when adding a filling material to the tooth.

Proper eye protection is also very important in the healthcare field. In dentistry, harmful wavelengths of light are used on a daily basis. When viewed directly with the eyes, dental curing lights that are used to polymerize certain filling materials are damaging to the dentist's eyesight. These lights typically emit wavelengths within the 400-500 nm range. One present solution to this problem is to place an orange filtering shield around the source of the curing light to reduce the amount of damaging light being exposed to the eyes. However, this shield is bulky and often does not fully protect the user's eyes. Another present solution applied by most dentists is to look away from the light, after the light has been positioned next to the patient's tooth and switched on. However, when the dentist is not looking at the position of the light, it is very easy for the dentist's hand and curing light to drift away from the tooth. This may lead to inadequate polymerization of the filling. With the eyewear in this application, the cameras can point directly toward the curing light, thus allowing the dentist to look at the area being cured on the video displays (SR, SL) without damaging the eyes. Sight filters (FR, FL) also can be activated for further protection against dental curing lights. This allows for both eye protection and operating precision.

Modern-day dentistry also involves laser usage of various wavelengths. These wavelengths may range from 450 nm to 10,600 nm, depending on the procedure being performed. These lasers require the dentist, patient, and adjacent staff members to wear wavelength-specific protective eyewear when in use. The eyewear of this patent application can have viewing windows (WR, WL) with various wavelength filtering options (FR, FL) controlled by voice activation or by an external device, to provide adequate protection while using a variety of lasers. For example, the user can specify that he wants all wavelengths between 450-655 nm filtered out of the viewing windows, or all wavelengths over 9300 nm to be filtered out. The user may also detach and switch out the viewing windows of this eyewear with wavelength-specific protective viewing windows of their choosing. Another option is to add external filters over the viewing windows.

While specific embodiments of the invention have been illustrated and described herein, it is realized that other modifications and changes will occur to those skilled in the art. It is therefore to be understood that the appended claims are intended to cover all modifications and changes that fall within the true spirit and scope of the invention.

What is claimed is:

1. An eyewear capable of viewing objects or patients below eye level at a Working Declination Angle (WDA) of 60 degrees or larger, wherein WDA is defined as the angle between the horizontal plane and the line from the viewer's eyes to the working area, where the horizontal plane is used to approximate a viewer's unstrained, straight viewing direction while sitting or standing with ergonomically healthy posture, said eyewear comprises:
   a right-eye video display device that displays the video image viewed by the right eye of the user;
   a left-eye video display device that displays the video image viewed by the left eye of the user, where the right-eye video display device and the left-eye video display device are placed at or near a horizontal orientation in front of the user, so that the user is able to view objects or patients located below eye level on the video display devices, while working with ergonomically healthy sitting or standing posture and with minimal to no straining of the eyes, wherein the right-eye and left-eye video display devices can be separate devices, or can also be combined into one video display device that has part of its structure used as the right-eye video display device and another part of its structure used as the left-eye video display device;
   a right-eye-side camera that is placed on or near the right-eye-side of the eyewear with a declination angle that is adjustable to be 60 degrees or larger, wherein declination angle is defined as the angle between the eyewear viewing direction and the viewing direction of the camera;
   a left-eye-side camera that is placed on or near the left-eye-side of the eyewear with a declination angle that is adjustable to be 60 degrees or larger, where the declination angle of the left-eye-side camera and the declination angle of the right-eye-side camera are adjusted to approximate the WDA of the user;
where the video images captured by the right-eye-side camera and the video images captured by the left-eye-side camera are processed and displayed on the right-eye video display device and the left-eye video display device, so that the user can see a three-dimensional view with accurate depth perception of objects or patients located below eye level, while maintaining ergonomically healthy sitting or standing posture.

2. The distance between the right-eye-side camera and the left-eye-side camera of the eyewear in claim 1 is adjustable to be about the same as the distance between the pupils of the user.

3. The video display devices of the eyewear in claim 1 are transparent or partially transparent while not in use.

4. The video display devices of the eyewear in claim 1 can be moved out of sight while not in use.

5. The eyewear in claim 1 includes light filters that can protect the user's eyes from damaging wavelengths of light.

6. The light filters in claim 5 can protect the user's eyes by filtering out the damaging wavelengths of light emitted by dental curing lights.

7. The light filters in claim 5 can protect the user's eyes by filtering out the damaging wavelengths of light emitted by laser devices.

8. The eyewear in claim 1 allows a user to look at an area being exposed to eye-damaging wavelengths of light on the video displays, such as dental curing lights or infrared lights, without damaging the eyes of the user.

9. The eyewear in claim 1 further comprises a pair of microphones.

10. The eyewear in claim 1 further comprises a pair of earphones.

11. The eyewear in claim 1 further comprises a light source with a light filter.

12. The eyewear in claim 1 supports zoom-in and zoom-out functions by displaying three-dimensional video images of variable magnification factors on the right-eye video display device and the left-eye video display device.

13. The eyewear in claim 1 supports size measurements for objects viewed by the right-eye-side camera and left-eye-side camera.

14. The eyewear in claim 1 is able to support picture-in-picture functioning with overlapping images of the same view at different magnification factors.

15. The eyewear in claim 1 is able to display previously recorded images, notes, figures or tables over the current viewing image.

16. The eyewear in claim 1 is able to overlap an infrared image over the current viewing image.

17. The eyewear in claim 1 is able to overlap a previously recorded three-dimensional radiology image over the current viewing image.

18. The eyewear in claim 1 supports teleconferencing so that other people can view the same three-dimensional view that the user is viewing.

19. The eyewear in claim 1 supports teleconferencing with voice communication.

20. The functions of the eyewear in claim 1 can be controlled by voice activated commands.

* * * * *